United States Patent [19]

Katsuyama et al.

[11] Patent Number: 4,671,937
[45] Date of Patent: Jun. 9, 1987

[54] MULTILAYER ANALYTICAL ELEMENT

[75] Inventors: Harumi Katsuyama; Fuminori Arai; Takushi Miyazako; Shigeru Nagatomo, all of Asaka, Japan

[73] Assignee: Fuji Photo Film Co., Ltd., Japan

[21] Appl. No.: 626,743

[22] Filed: Jul. 2, 1984

[30] Foreign Application Priority Data

Jun. 30, 1983 [JP] Japan .................... 58-118594

[51] Int. Cl.⁴ .............. G01N 1/48; C12R 1/585; C12R 1/64; C12R 1/59
[52] U.S. Cl. ............................. 422/56; 436/518; 436/810; 436/903; 436/904; 436/910; 435/4; 435/22; 435/805; 422/57; 427/3
[58] Field of Search .............. 436/518, 810, 904, 903, 436/910; 435/4, 22, 805; 422/56; 427/3

[56] References Cited

U.S. PATENT DOCUMENTS 3,992,158 11/1976 Przybylowicz et al. .......... 23/253
4,404,286 9/1983 Shull ................................. 436/97
4,576,793 3/1986 Koyama et al. .................. 422/56

FOREIGN PATENT DOCUMENTS 0031699 2/1984 Japan .

OTHER PUBLICATIONS

Chemical Abstracts, vol. 76, #128954A, 1972.
Chemical Abstracts, vol. 75, #37386E, 1971.

Primary Examiner—Christine M. Nucker
Assistant Examiner—Patricia L. DeSantis
Attorney, Agent, or Firm—Toren, McGeady and Goldberg

[57] ABSTRACT

A multilayer analytical element for analysis of analyte in a liquid sample comprising a liquid sample-spreading layer, a reagent layer containing a diazonium salt, and a liquid-impermeable light-transmissive support, being laminated in this order, in which said reagent layer contains a sulfonic acid group-containing polymer having at least 10 molar % of a repeating unit selected from those consisting of a sulfoalkyl group and sulfophenyl group. The analytical element can be an element comprising a porous reagent layer containing a diazonium salt and the liquid-impermeable light-transmissive support, being laminated in this order.

13 Claims, 1 Drawing Figure

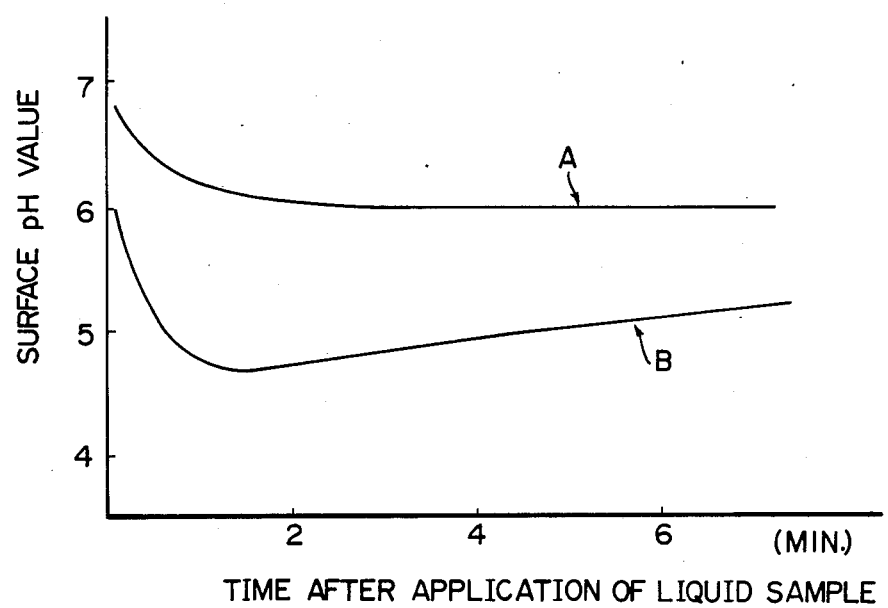

MULTILAYER ANALYTICAL ELEMENT

BACKGROUND OF THE INVENTION

1. Field of the Invention

The present invention relates to a multilayer analytical element, and more particularly to an analytical element appropriately employable for dry analysis of substance contained in a body fluid including substance contained therein in micro-quantity.

2. Description of Prior Arts

As a method of analysis of substance contained in a liquid sample such as a body fluid, there has been heretofore utilized a wet analysis such as a method comprising a step of bringing said substance into contact with other substance (reagent) contained in a certain solvent so as to cause a detectable reaction such as a reaction directly or indirectly showing color-formation or color-change, and a step of detecting said reaction.

On the other hand, a dry analysis (i.e., dry analysis operation) developed for the purpose of simplifying the analytical procedures has been recently utilized. As a representative example of an analytical element utilized for the dry analysis, well known is a dry analytical element (also called dry analytical material or article) which is in the form of a sheet, film, strip or tape comprising basically a spreading layer for spreading a liquid sample containing substance to be detected (i.e., analyte), at least one reagent layer containing a reagent which directly or indirectly gives a certain detectable reaction in contact with the analyte, and a light-transmissive support. The analysis employing the multilayer analytical element is generally carried out by procedures of applying a liquid sample containing the analyte onto the liquid sample-spreading layer of the analytical element, subjecting the analytical element to incubation if necessary, detecting the resulting detectable reaction such as generation (formation) or change of color by a photometric means or the like, and determining amount of the analyte according to colorimetry.

There are known a variety of analytical systems utilizable in analysis of analyte employing the multilayer analytical element. Representative examples of the analytical systems are as follows.

(A) An analytical system for detecting and measuring a detectable reaction occurring between a reagent contained in the reagent layer and the analyte, such as a reaction showing generation or change of color. This analytical system is employable for analyses of analytes such as a variety of proteins, for instance, total protein, albumin and globulin, hemoglobin decomposition substances, for instance, free (i.e., non-conjugated or indirect) bilirubin and conjugated (i.e., direct) bilirubin.

(B) An analytical system employing a reagent layer containing at least two kinds of reagents, which comprises procedures of causing reaction between one of the reagents and the analyte to produce a reactive substance such as ammonia or hydrogen peroxide, bringing the reactive substance in contact with other reagent (e.g., dye precursor) to cause a detectable reaction such as generation or change of color, and detecting and measuring the reaction. This analytical system is employable for analysis in the case that the analyte is glucose; lipid such as cholesterol, triglyceride and free fatty acid; enzyme such as lactate dehydrogenase; urea and uric acid.

(C) An analytical system employing a reagent layer containing a non-diffusive reagent having a color-forming group, which comprises procedures of converting the reagent into a diffusive product carrying the color-forming group by reaction with analyte, separating the diffusive product from the unreacted non-diffusive reagent, causing a detectable reaction such as generation or change of color by bringing the diffusive product into contact with a chromogen substance such as coupler, and detecting and measuring the reaction. This analytical system is employable for analysis of polysaccharide hydrolase such as amylase.

(D) An analytical system employing a reagent layer containing a non-diffusive reagent having a detectable character (e.g., color), which comprises procedures of producing a diffusive product carrying the detectable character from the reagent through reaction with the analyte, separating the diffusive product from the unreacted non-diffusive reagent, and detecting and measuring the diffusive product. This analytical system is employable for analysis of polysaccharide hydrolase such as amylase.

As described above, the multilayer analytical element contains a reagent reactive to analyte and may further contain other reagent reactive to a product given by reaction between the analyte and the above-mentioned reagent. These reagents are selected appropriately to meet the purposes of analysis. Among these reagents, not a few kind of reagents easily deteriorate under certain surrounding conditions, such as light, heat, and pH condition. Further, some reagents need specific pH condition to show their reactivities, and hence these reagents should be used under specific surrounding pH condition.

As described above, one of the representative analytical systems includes detecting color generation or color change caused by the reaction between a color-forming regent and an analyte or a reaction product of the analyte with other reagent, said color-forming reagent and other reagent both being beforehand incorporated into the analytical element. As the color-forming reagent (i.e., dye precursor) for the analyses of various analytes according to the above-stated analytical system, a diazonium salt is generally employed because the diazonium salt undergoes very sensitive reaction and is easily available. However, the diazonium salt has a drawback in that the diazonium salt is decomposed upon exposure to light. It has been heretofore known that the diazonium salt is easily decomposable upon exposure to light but is relatively stable in a low pH range, namely, on the acidic side. Hence, it has been proposed that the diazonium salt be preserved in the presence of an acidic substance. Particularly, a carboxylic acid type polymer that can serve as a binder to form a diazonium salt-containing layer, providing an acidic condition, is generally employed in combination with the diazonium salt to prepare an analytical element containing a diazonium salt. However, the use of the carboxylic acid type polymer is not sufficiently effective to stabilize the diazonium salt.

SUMMARY OF THE INVENTION

As a result of the study for finding materials which are effective for stabilization of a diazonium salt in a multilayer analytical element utilizing the diazonium salt as an analytical reagent or one component of analytical reagents, the present inventors have discovered that the diazonium salt can be preserved with high stabilization in contact with a polymer having at least 10 molar % of a repeating unit selected from those consisting of a sulfoalkyl group and sulfophenyl group.

Accordingly, the present invention resides in a multilayer analytical element for analysis of analyte in a liquid sample comprising a liquid sample-spreading layer, a reagent layer containing a diazonium salt, and a liquid-impermeable light-transmissive support, being laminated in this order, in which said reagent layer contains a sulfonic acid group-containing polymer having at least 10 molar % of a repeating unit selected from those consisting of a sulfoalkyl group and sulfophenyl group.

According to another embodiment of the invention, the combination of said liquid sample-spreading layer and said reagent layer containing a diazonium salt both constituting a part of the elementary structure of the mulytilayer analytical element can be replaced with a single porous reagent containing a diazonium salt. More in detail, if the diazonium salt-containing reagent layer is made porous, the reagent layer also can serve as the liquid sample-spreading layer. Further, the diazonium salt-containing reagent layer can be made porous to such an extent that the porous structure is able to allow permeation of a high molecular weight analyte such as bilirubin or enzyme into the reagent layer.

The sulfonic acid group-containing polymer having a repeating unit selected from those consisting of a sulfoalkyl group and sulfophenyl group employed in the present invention provides a preferable surrounding pH condition for preserving a diazonium salt in a multilayer analytical element, as well as serves effectively as a binder of the diazonium salt. Therefore, said polymer is advantageously employed for the formation of a diazonium salt-containing reagent layer in the preparation of a multilayer analytical element utilizing a diazonium salt as a detector reagent, for instance, an analytical element for analysis of bilirubin.

The above-mentioned sulfonic acid group-containing polymer is also effectively employable for the stabilization of a diazonium salt during its preservation in a multilayer analytical element designed for analysis of enzyme or enzyme substrate, in which the analysis comprises enzyme reaction of analyte, for example, an enzyme or an enzyme substrate such as amylase or an amylase substrate, and subsequent quantitative determination of the amount of the reaction product (e.g., oligosacchride or glucose attached with a coupler of diazonium salt) through measurement of the color density of a dye produced by reaction of the diazonium salt and the reaction product.

In the case that the above-mentioned sulfonic acid group-containing polymer is employed for stabilization of a diazonium salt contained in a reagent layer of a multilayer analytical element for analysis of enzyme or enzyme substrate, a nondiffusive base-containing layer capable of adjusting in conjunction with said reagent layer the pH condition surrounding the diazonium salt at the time of progress of its reaction is preferably attached to said reagent layer through liquid contact. The provision of the nondiffusive base-containing layer is particularly important in the case that there is difference between the pH condition (acidic condition) for stable preservation of the contained diazonium salt and the pH condition for allowing smooth progress of the objective enzyme reaction.

More in detail, while an enzyme reaction involving amylase proceeds smoothly under neutral or basic condition, such surrounding condition is adverse to the pH condition being appropriate for stable preservation of a diazonium salt. In such case, if a nondiffusive base-containing layer is attached through liquid contact to the reagent layer retaining a diazonium salt under acidic condition by the incorporation of a sulfonic acid-containing polymer so as to allow adjusting in conjunction with the reagent layer the pH condition surrounding the diazonium salt at the time of progress of its reaction, the reagent layer is kept under acidic condition prior to introduction of a liquid sample containing analyte into the multilayer analytical element, while the pH condition of the reagent layer turns neutral or basic after introduction of the liquid sample thereinto through buffer reaction caused by liquid contact of the nondiffusive base-containing layer to the reagent layer. Thus, there can be obtained a multilayer analytical element in which the diazonium salt is preserved stably and the objective enzyme reaction proceeds smoothly, by utilizing a combination of the diazonium salt-containing reagent layer which is made acidic by incorporation of the sulfonic acid group-containing polymer and the nondiffusive base-containing layer.

Moreover, the sulfonic acid group-containing polymer employed in the present invention is advantageously effective in readily providing stable pH condition in conjunction with the above-mentioned nondiffusive base-containing layer. Accordingly, the sulfonic acid group-containing polymer is of value as a binder of a multilayer analytical element and further as a pH conditioner.

BRIEF DESCRIPTION OF DRAWINGS

FIG. 1 graphically illustrates an example of the pH adjusting power observed in a multilayer analytical element according to the present invention. In the graph, A is a curve representing pH change on the surface of the liquid sample-spreading layer after spotting a liquid sample observed in the use of a multilayer analytical element of the invention, and B is a curve representing pH change on the surface of the liquid sample-spreading layer after spotting a liquid sample observed in the use of a multilayer analytical element for comparison.

DETAILED DESCRIPTION OF THE INVENTION

The multilayer analytical element comprises a basic structure consisting essentially of a liquid sample-spreading layer, one or more reagent layers, and liquid-impermeable light-transmissive support, being laminated in this order.

In the above-mentioned basic structure, the liquid sample-spreading layer and the light-transmissive support both are known with respect to their materials and constitutions. Accordingly, the liquid sample-spreading layer and the light-transmissive support employed for constituting the multilayer analytical element of the present invention can be optionally formed utilizing these known materials and constitutions.

The reagent layer of the multilayer analytical element of the present invention contains a diazonium salt having a function as a reagent for direct or indirect detection of analyte and a sulfonic acid group-containing polymer. The reagent layer may be a porous or nonporous reagent layer. The diazonium salt-containing porous reagent layer can be prepared by incorporating both the diazonium salt and the sulfonic acid group-containing polymer, as well as one or more other reagents if desired, into a substrate known as material of a liquid sample-spreading layer such as woven fabric or nonwoven fabric. Otherwise, the porous reagent layer may be in the form of a porous matrix layer consisting essentially of fine particulate organic or inorganic material bonded with the sulfonic acid group-containing polymer and containing the diazonium salt.

In the present invention, the reagent layer of the multilayer analytical element preferably is in the form of a porous reagent layer containing a diazonium salt.

There is no specific limitation on the diazonium salt to be incorporated into the reagent layer of the multilayer analytical element of the invention, as far as it can be employed in the analytical element for the direct or indirect detection of a variety of analytes. Examples of the diazonium salt include chlorides of 2,5-dimethoxybenzenediazonium, p-(dimethylamino)benzenediazonium, p-(cyclohexylamino)benzenediazonium, 2,5-dimethoxy-4-morpholinobenzenediazonium, 2-methoxy-5-dodecyloxycarbonylbenenediazonium, p-sulfobenzenediazonium and 2-methoxy-5-[β-(2,4-di-t-amylphenoxy)ethoxycarbonyl]-benzenediazonium; and tetrafluoroborates, hexafluoroborates, hexafluoroaluminates, trichlorozincates and p-toluenesulfonates of the above-mentioned diazonium. The detailed descriptions on the diazonium salts mentioned above and other employable diazonium salts are given in "Light Sensitive Systems" written by Jaromir Kosar (John Wiley & Sons, Inc., 1965).

The diazonium salt employed in the present invention may be attached to a polymer such as starch or other compound.

The sulfonic acid group-containing polymer to be incorporated into the reagent layer of the analytical element of the invention is a polymer having at least 10 molar % (preferably at least 30 molar %) of a repeating unit selected from those consisting of a sulfoalkyl group and sulfophenyl group. The sulfonic acid group containing polymer preferably is a homopolymer of a repeating unit selected from those consisting of a sulfoalkyl group and sulfophenyl group.

A representative example of the repeating unit having sulfoalkyl group is a repeating unit represented by the formula (I):

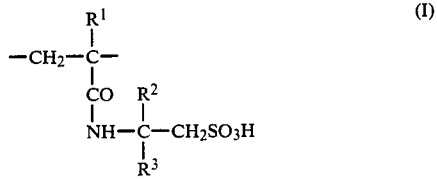

in which $R^1$ and $R^2$ are the same or different and each represents hydrogen atom or methyl group, and $R^3$ represents an alkyl group having 1–18 carbon atoms, an aryl or alkyl-substituted aryl group having 6–10 carbon atoms, or an alkoxycarbonyl group having 1–5 carbon atoms.

In the above formula (I), $R^3$ preferably is an alkyl group having 1–8 carbon atoms, phenyl group or methoxycarbonyl group. Particularly preferred are methyl, ethyl and propyl groups.

The monomer giving the repeating unit of the above-mentioned formula (I) can be readily prepared by a knwon method or a method onologous to the known method. For instance, the preparations of various monomers having hydrogen atom as $R^1$ are described in the specification of U.S. Pat. No. 3,506,707.

Examples of the monomer giving the repeating unit of the formula (I) include N-(sulfoalkyl)acrylamide, [preferably N-(β-sulfo-t-butyl)acrylamide, etc.], and N-(sulfoalkyl)methacrylamide [preferably N-(β-sulfo-t-butyl)methacrylamide].

In the present invention, a representative example of the monomer giving a repeating unit having sulfophenyl group is p-styrenesulfonic acid.

In the case that the sulfonic acid group-containing polymer having a repeating unit of sulfoalkyl group is a copolymer, said copolymer may be a copolymer of a monomer of the formula (I) and other monomer copolymerizable with said monomer. Examples of the copolymerizable monomer include olefins such as ethylene and propylene; acrylic acid and its derivatives such as acrylic acid esters (e.g., methylester and ethylester), acrylic acid hydroxyalkylesters (e.g., hydroxyethylester) and acrylamide; methacrylic acid and its derivatives such as methacrylic acid esters (e.g., methylester, ethylester, butylester, isobutylester, hexylester), methacrylic acid hydroxylalkylesters (e.g., hydroxyethylester) and methacrylamide; and double bond-containing dicarboxylic acids such as meleic acid and fumaric acid.

Examples of the homopolymer include poly(2-acrylamido-2-methylpropanesulfonic acid) and poly(2-methacrylamido-2-methylpropanesulfonic acid).

The above-mentioned sulfonic acid group-containing polymers can be easily prepared by referring to the description given in "Synthesis of Polymers I" editted by C. G. Overberger or "Experimental Text of Polymer Synthesis" (Takayuki Ohtsu & Masayoshi Kinosita, 1972, Kagaku Dozin, Japan).

In the case of the copolymer having the repeating unit of sulfophenyl group, the monomer copolymerizable with the monomer having sulfophenyl group which is employable for the preparation thereof can be the same as described above.

The sulfonic acid group-containing polymer to be contained in the reagent layer can serve as such a binder of the reagent layer. Therefore, a most simple reagent layer of the multilayer analtyical element of the invention can be a layer of the sulfonic acid group-containing polymer in which a diazonium salt is uniformly dispersed. Other embodiments of the reagent layer include a layer of a mixture of the sulfonic acid-group containing polymer and other polymer such as a carboxylic acid type polymer in which a diazonium salt is uniformly dispersed. The reagent layer may contain one or more reagent other than the diazonium salt.

The multilayer analytical element of the present invention may have one or more of functional layers known in the structures of the conventional multilayer analytical elements, for example, a light-reflecting layer, a light-blocking layer, a diffusion-preventing layer, and an adhesive layer (to be attached to the reagent layer).

Moreover, a multilayer analytical element for analysis of enzyme such as amylase or enzyme substrate may have a substrate-containing layer or an enzyme-containing layer in addition to the reagent layer. In such case having the substrate-containing layer or the enzyme-containing layer, a nondiffusive base-containing layer is preferably provided in the element, preferably in a position adjacent to one of these layers or the reagent layer. The nondiffusive base-containing layer is advantageously provided in such a manner that the nondiffusive base-containing layer can adjust in conjunction via liquid contact with the reagent layer containing the sulfonic acid group-containing polymer and a diazonium salt the pH condition surrounding the diazonium salt at the time of progress of its reaction.

The nondiffusive base to be incorporated into the above-mentioned nondiffusive base-containing layer preferably is a basic polymer. Examples of the basic polymer include a homopolymer and copolymer of an unsaturated monomer selected from the group consisting of 2-vinylpyridine, 4-vinylpyridine, N-vinylimidazole, 1-vinyl-3-alkyl-2,3-dihydroimidazole (i.e., 1-vinyl-3-alkyl-4-imidazoline) [preferably 1-vinyl-3-ethyl-2, 3-dihydroimidazole, 1-vinyl-3-methyl-2, 3-dihydroimidazole, 1-vinylbenzyl-2,3-dihydroimidazole, etc.], 2-vinyl-1-alkylimidazole, 3-[preferably 2-vinyl-1-methylimidazole, 2-vinyl-1-ethylimidazole, 2-vinyl-1-benzylimidazole, etc.](dialkylamino)alkyl acrylate [preferably $\beta$-(dimethylamino) methyl acrylate, $\beta$-(dimethylamino)ethyl acrylate, $\beta$-(diethylamino)ethyl acrylate, $\beta$-morpholinoethyl acrylate. $\gamma$-(dimethylamino)propyl acrylate, etc.], (dialkylamino) alkyl methacrylate [preferably $\beta$-(dimethylamino)-methyl methacrylate, $\beta$-(dimethylamino)ethyl methacrylate, $\beta$-(diethylamino)ethyl methacrylate, $\beta$-morpholinoethyl methacrylate, $\gamma$-(dimethylamino)propyl methacrylate, etc.], N-[(dialkylamino)alkyl]acrylamide [preferably N-[(dimethylamino)propyl]acrylamide, etc.], and N-[(dialkylamino)alkyl]methacrylamide [preferably N-[(dimethylamino) propyl]methacrylamide, etc.], or a copolymer of the unsaturated monomer with other unsaturated monomer or monomers.

Examples of the "other unsaturated monomer" given above for the basic polymer include styrene, divinylbenzene, acrylamide, N-substituted acrylamide, methacryliamide, N-substituted methacrylamide, acrylic acid ester, methacrylic acid ester, and N-vinylpyrrolidone.

The basic polymer may be employed singly or in combination, and further may be employed in combination with other polymers, for example, water-soluble polymer or polymers such as gelatin and polyvinyl alcohol or aqueous latex of hydrophobic polymer or polymers.

As described hereinbefore, the combination of the liquid sample-spreading layer and the diazonium salt-containing reagent layer constituting the basic structure of the multilayer analytical element of the present invention can be replaced with a porous reagent layer containing a diazonium layer. In other words, if the reagent layer containing both the diazonium salt and the sulfonic acid group-containing polymer is replaced with the porous reagent layer, the provision of the liquid sample-spreading layer can be omitted.

The following examples will further describe the present invention.

EXAMPLE 1

Multilayer Analytical Element for Analysis of Bilirubin (1) Preparation of Multilayer Analytical Element An aqueous gelatin solution was coated on a surface of a transparent polyethylene terephthalate (PET) support (thickness 180$\mu$m) and dried to give a coating layer having dry weight of 14 g/m$^2$. The gelatin layer was then wetted with water, and subsequently a cotton broadcloth (80 count) was pressed onto the wet gelatin layer to give a laminated structure. On the surface of the laminated structure was applied a coating solution for the formation of reagent layer which comprised 4 g. of p-sulfobenzenediazonium p-toluenesulfonate, 150 g. of dyphylline[CAS Reg. No. 479-18-5], 200 ml. of 5% aqueous poly(2-acrylamido-2-methylpropylanesulfonic acid) solution, 950 ml. of water, and 0.5 g. of nonionic surfactant (octylphenoxy-polyethoxyethanol) in an amount of 100 ml/m$^2$ so that the coating solution was incorporated into the broadcloth layer. Subsequently, the broadcloth layer was dried to give a multilayer analytical element (or multilayer analytical film) for quantitative analysis of bilirubin.

(2) Analysis of Bilirubin

On the surface of the diazonium salt-containing cotton broadcloth (porous reagent layer) of thus prepared multilayer analytical element for bilirubin analysis (hereinafter termed Analytical Element I) was spotted 10 $\mu$l. of each of comercial control serums having different bilirubin concentrations. Analytical Element I was then incubated at 37° C. for 5 min., and the reflection density was measured at wavelength of 540 nm by reflection photometry from the PET support side.

The results are set forth in Table 1.

TABLE 1

| Bilirubin Concentration | Optical Density (OD) |
| --- | --- |
| 1.58 (mg/dl) | 0.206 |
| 4.17 | 0.275 |
| 10.9 | 0.389 |
| 20.1 | 0.591 |

The results set forth in Table 1 indicate that Analytical Element I is a satisfactory multilayer analytical element employable for quantitative analysis of bilirubin.

(3) Preservation Stability of Multilayer Analytical Element

The above-mentioned Analytical Element I was sufficiently dried in vacuo and immediately wrapped in a moisture-proof material. Thus wrapped element was then kept at 35° C. for 2 weeks.

Further, a multilayer analytical element for comparison (Analytical Element II) was prepared by repeating the above-described method for the preparation of Analytical Element I except that 200 ml. of the 5% aqueous poly(2-acrylamido-2-methylpropanesulfonic acid) solution was replaced with the same amount of 5% aqueous solution of methyl vinyl ether - maleic anhydride (1:1, molar ratio) copolymer (GANTREZ AN 139, tradename of GAF, inherant viscosity [$\eta$]=1.0–1.4). Thus prepared Analytical Element II was also sufficiently dried in vacuo and immediately wrapped in a moisture-proof material. Thus wrapped element was then kept at 35° C. for 2 weeks.

Independently, Analytical Elements I and II were kept under the dry and vacuum conditons in the same manner at 4° C. for 2 weeks.

The bilirubin control serum having the same concentration as above was applied onto Analytical Element I and Analytical Element II (comparison sample) before and after the high temperature storage as well as before and after the low temperature storage. The color formation was then measured in the same manner as above, and the results were compared between each other. The results are set forth in Table 2, in which the numerical value is color density ratio calculated according to the following equation.

$$\text{Color Density Ratio (\%)} = \frac{\text{Color Density of Element After Storage}}{\text{Color Density of Element Before Storage}} \times 100$$

TABLE 2

| Sample | Color Density Ratio | |
|---|---|---|
| | 35° C. Preservation | 4° C. Preservation |
| Analytical Element I | 95% | 100% |
| Analytical Element II | 72% | 99% |

EXAMPLE 2

Multilayer Analytical Element for Determination of Amylase Activity (1) Preparation of Multilayer Analytical Element A multilayer analytical element for determination of amylase activity was prepared to have a structure of a support, a basic polymer layer, a color reaction layer (reagent layer) containing sulfonic acid group-containing polymer, a light-shielding layer, a coupler substrate layer, and a liquid sample-spreading layer, being laminated in this order, using the materials and coating solutions shown below.

(1) Support

A transparent polyethylene terephthalate (PET) film (thickness 180 μm) provided with a gelatin subbing layer:

(2) Basic Polymer Layer

| Formulation of coating solution of formation of basic polymer layer | |
|---|---|
| Alkaline-treated gelatin | 2 g. |
| Poly(N—vinylimidazole) | 5 g. |
| Water | 60 g. |
| Polyoxyethylene nonylphenyl ether (containing 10 oxyethylene groups in one molecule on average) | 0.2 g. |

The formulated coating solution was coated over a support and then dried to form a basic polymer layer (thickness 15 μm).

(3) Color Reaction Layer (Reagent Layer)

There was prepared 100 ml. of 5% aqueous solution of β-hydroxypropyl methacrylate - N-(α, α-dimethyl-β-sulfoethyl) acrylamide (6:4) copolymer as a binder solution.

Independently, 0.150 g. of 2-methoxy-5-[β(2,4-di-t-amylphenoxy) ethoxycarbonyl]benzenediazonium tetrafluoroborate was dissolved in a mixture of 2 ml. of acetone and 4 ml. of ethyl alcohol to prepare a diazonium salt solution. The diazonium salt solution was then added to the binder solution under stirring. After the addition was complete, the resulting mixture solution (coating solution for the formation of color reaction layer) was observed for 20 min. The resulting solution was kept transparent.

The coating solution (for the formation of color reaction layer) was coated on the aforementioned basic polymer layer and dried in air at 50° C. to form a dry color reaction layer of 3 μum thick. The dry color reaction layer was highly transparent.

(4) Light-Shielding Layer

A mixture of 50 ml. of water, 80 g. of particulate titanium dioxide, 0.5 g. of p-nonylphenoxyglycerol (25 % aqueous solution), and 300 g. of 8% gelatin was sufficiently pulverized in a ball mill-type pulverizer. The resulting dispersion was coated on the color reaction layer and dried to form a light-shielding layer. Thus formed light-shielding layer had thickness of 6 μm after dryness.

(5) Coupler Substrate Layer

A solution was prepared by mixing 10 g. of the coupler starch (number of reactive coupler molecules/number of glucose units=1/30SO) in which the reactive coupler was 2[8-hydroxy-3,6-bis(sodium sulfonato)-1-naphthylamino]-4,6-dichloro-s-triazine prepared from cyanuric chloride and 1-amino-8-hydroxynaphthalene-3,6-disulfonic acid monosodium salt according to a method described by J. T. Thurstton et al., in J. Amer. Chem. Soc., 73(7), 2981-29(1951), 105 g. of water, 8 g. of polyacrylamide (5% aqueous solution), and 2 g. of p-nonylphenoxyglycerol (25% aqueous solution). The resluting solution was filtrated over a nylon-mesh sheet filter to prepare a coating solution for forming the coupler substrate layer. Thus prepared solution was coated and dried on the light-shielding layer to form the coupler substrate layer having thickness of 10 μm (after dryness).

(6) Liquid Sample-Spreading Layer

A mix-spinned fabric of polyester (polyethylene terephthalate and cotton (mixed rate: polyester/cotton =75/25) was impregnated with an aqueous solution consisting of 150 g. of polyacrylamide (mean polymerization degree: 18,000, 0.8% aqueous solution) and 1 g. of p-nonylphenoxyglycerol 25 aqueous solution) to prepare a hydrophilic fabric.

A surface of the coupler substrate layer prepared as above was wetted with p-nonylphenoxyglycerol 0.2 % aqueous solution), and then the hydrophilic fabric was laminated on the surface of the coupler substrate layer under pressure, and finally dried.

(2) Evaluation of Analytical Element for Determination of Amylase Activity

The multilayer analytical element for determination of amylase activity prepared as above (hereinafter termed Analytical Element III) was evaluated in the following manner.

Fresh human saliva was diluted with a 7% albumin physiological saline solution to prepare amylase standard liquids having activity values of 500, 1,000 and 2,000 IU/l. 10 μl of the amylase standard liquid was spotted onto the liquid sample-spreading layer of the above-mentioned Analytical Element III to perform hydrolysis reaction at 37° C. After 10 min., the color density was measured at wavelength of 550 nm by obtaining reflection optical density of the color reaction layer of the analytical element from the PET side using a Macbeth Reflection Densitometer.

The results of the measurement of amylase activity on Analytical Element III are set forth in Table S. The reflection optical density value of the color reaction layer given in Table S is expressed by difference between the observed value and the blank value (reflection optical density observed in the case that 7% aqueous albumin solution containing no amylase was spotted on the liquid sample-spreading layer).

TABLE 3

| Amylase Activity | Reflection Optical Density |
|---|---|
| 500 IU/l | 0.14 |
| 1,000 IU/l | 0.40 |

TABLE 3-continued

| Amylase Activity | Reflection Optical Density |
|---|---|
| 2,000 IU/l | 0.66 |

(3) Preservation Stability of Multilayer Analytical Element

A multilayer analytical element for comparison (Analytical Element IV) was prepared by repeating the above-described method for the preparation of Analytical Element III except that the binder solution was replaced with the carboxylic acid type polymer binder solution set forth below.

To 100 ml. of water were added 5 g. of carboxylic acid type polymer [methyl vinyl ether - maleic anhydride copolymer (1:1, molar ratio, GANTREZ AN 139, tradename of GAF, inherent viscosity $[\eta]=1.0$–1.4)] and 1 g. of polyoxyethylenenonylphenol (mean number of oxyethylene group in molecule: 10). The resulting mixture was heated at 80° C. for 30 min. to undergo esterification reaction. Thus, a binder solution was obtained.

Analytical Element III and Analytical Element IV (comparison sample) both were heated at 45° C. for 3 days. Both elements were then evaluated by measuring the color-forming rate of the diazonium salt on the color reaction layer in the same manner as in Example 1 using the same amylase standard solution as above. Independently, the color-forming rates on the color reaction layers of Analytical Elements III and IV prior to the heat treatment were measured in the same manner. From these measured values, the color-forming rate ratio (%) [=100×color-forming rate after heat treatment/color forming rate before heat treatment] was calculated. The results are set forth in Table 4.

TABLE 4

| Analytical Element | Color-Forming Rate Ratio |
|---|---|
| Analytical Element III | 92% |
| Analytical Element IV | 35% |

(4) Measurement of Formation of Background Fog

Each of Analytical Element III and Analytical Element IV (comparison sample) was placed at 1 meter distance from a 30 W fluorescent lamp to expose to the lamp for 5 hours. Increase of the background fog on Analytical Element III was 0.02, while that on Analytical Element IV was 0.28.

(5) Evaluation of pH Adjusting Power

On the liquid sample-spreading layer of each of Analytical Element III and Analytical Element IV (comparison sample) was spotted 10 μl. of Versatol (control serum, Werner-Lambert Corp., pH=7.3), and the change of pH value (surface pH value of the liquid sample-spreading layer) with the passage of time after spotting on the liquid sample-spreading layer was measured. The results are illustrated in FIG. 1.

As seen from FIG. 1, Analytical Element III showed little pH value change on the surface of the liquid sample-spreading layer after the spotting, and the pH value at approx. 1.5 to 2.0 min. after the spotting was stable. In contrast, Analytical Element IV showed great fluctuation of pH value on the surface of the liquid sample-spreading layer until one minute from the spotting, and thereafter the pH value still varied.

These results indicate that the multilayer analytical element containing sulfonic acid group-containing polymer according to the present invention is satisfactory even in the pH adjusting power.

EXAMPLE 3

Multilayer Analytical Element for Determination of Amylase Activity (1) Preparation of Multilayer Analytical Element The process for the preparation of Analytical Element III described in Exmaple 2 was repeated except that the diazonium salt was changed to 2-methoxy-5-tetradecyloxycarbonylbenzenediazonium tetrafluoroborate and the polymer of a binder solution for the preparation of a color reaction layer was changed to the copolymer set forth in Table 5. Thus, Analytical Elements V, VI, VII, and VIII were prepared. Among them, Analytical Elements V, VI, and VII were samples according to the present invention, while Analytical Element VIII was for comparison.

TABLE 5

| Analytical Element | Copolymer |
|---|---|
| V | β-Hydroxypropyl methacrylate - N—(α,α-dimethyl-β-sulfoethyl)-acrylamide (6:4) copolymer |
| VI | N—(β-Aceto-α,α-dimethylethyl)-acrylamide - p-sulfostyrene (5:5) copolymer |
| VII | β-Hydroxyethyl methacrylate - p-sulfostyrene (3:7) copolymer |
| VIII | Methyl vinyl ether - maleic anhydride (5:5) copolymer |

(2) Background Fog and Color-Forming Rate: Change with the Passage of Time

Each of the multilayer analytical elements was measured on change with the passage of time concerning background fog and color-forming rate in the manner set forth below.

(i) Change of background fog with passage of time

The analytical element was preserved under heating 45° C. for 5 days and was subsequently subjected to reflection optical measurement from the PET support side at wavelength of 550 nm. The difference between thus measured reflection density and the reflection density measured prior to the heat treatment was calculated to give the change of background fog with the passage of time.

(ii) Change of color-forming rate with passage of time

The analytical element was preserved under heating at 45° C. for 5 days and was subsequently subjected to the measurement of color-forming rate upon spotting a coupler pentose prepared using maltose as substrate according to the aforementioned method proposed by J. T. Thurstton, et al. The ratio of the measured value to the corresponding value measured before the heat treatment (=100×color-forming rate after heat treatment/color-forming rate before heat treatment) was calculated and given as the change of the color-forming rate with the passage of time. The results are set forth in Table 6.

TABLE 6

| Analytical Element | Change with Passage of Time | |
|---|---|---|
|  | Background Fog | Color-Forming Rate |
| Analytical Element V | 0.12 | 90% |
| Analytical Element VI | 0.13 | 85% |
| Analytical Element VII | 0.15 | 87% |
| Analytical Element VIII | 0.24 | 35% |

We claim:

1. A multilayer analytical element for analysis of a substance in a liquid sample comprising a liquid sample-spreading layer, a reagent layer containing a diazonium salt, and a liquid-impermeable light-transmissive support, in which said reagent layer contains a polymer containing at least 10 molar % of a repeating unit having a sulfophenyl group, wherein said polymer provides a pH environment which preserves the diazonium salt in the reagent layer.

2. The analytical element of claim 1 in which said polymer contains not less than 30 molar % of the repeating unit having a sulfophenyl group.

3. The analytical element of claim 1 in which said polymer is a homopolymer consisting essentially of a repeating unit having a sulfophenyl group.

4. A multilayer analytical element for the analysis of a substance in a liquid sample comprising a liquid sample-spreading layer, a reagent layer containing a diazonium salt and a liquid-impermeable light-transmissive support, in which said reagent layer contains a polymer containing at least 10 molar % of a repeating unit selected from those consisting of a repeating unit having a sulfoalkyl group and a repeating unit having a sulfophenyl group, and in which a nondiffusive base-containing layer is provided under the condition that the nondiffusive base-containing layer is in liquid contact with said reagent layer, and wherein said polymer provides a pH environment which preserves the diazonium salt in the reagent layer.

5. The analytical element of claim 4 in which said nondiffusive base is in the form of a polymer.

6. The analytical element of claim 4 in which said polymer contains not less than 30 molar % of the repeating unit selected from those consisting of a repeating unit having a sulfoalkyl group and a repeating unit having a sulfophenyl group.

7. The analytical element of claim 4 in which said polymer is a homopolymer consisting essentially of a repeating unit selected from those consisting of a repeating unit having a sulfoalkyl group and a repeating unit having a sulfophenyl group.

8. A multilayer analytical element for analysis of a substance in a liquid sample comprising a porous reagent layer containing a diazonium salt and a liquid impermeable light-transmissive support, in which said porous reagent layer contains a polymer containing at least 30 molar % of a repeating unit having a sulfophenyl group, and wherein said polymer provides a pH environment which preserves the diazonium salt in the reagent layer.

9. The analytical element of claim 8 in which said polymer is a homopolymer consisting essentially of a repeating unit having a sulfophenyl group.

10. A multilayer analytical element for analysis of a substance in a liquid sample comprising a porous reagent layer containing a diazonium salt and a liquid impermeable light-transmissive support, in which which said porous reagent layer contains a polymer containng at leasts 30 molar % of a repeating unit selected from those consisting of a repeating unit having a sulfoalkyl group and a repeating unit having a sulfophenyl group, and in which a nondiffusive base containing layer is provided under the condition that the nondiffusive base-containing layer is in liquid contact with said porous reagent layer, and wherein said polymer provides a pH environment which preserves the diazonium salt in the reagent layer.

11. The analytical element of claim 10 in which said nondiffusive base is in the form of a polymer.

12. The analytical element of claim 10 in which the repeating unit is a repeating unit having a sulfophenyl group.

13. The analytical element of claim 10 in which said polymer is a homopolymer consisting essentially of a repeating unit selected from those consisting of a repeating unit having a sulfoalkyl group and a repeating unit having a sulfophenyl group.

* * * * *